(12) United States Patent
Basset et al.

(10) Patent No.: US 8,119,852 B2
(45) Date of Patent: Feb. 21, 2012

(54) PROCESS FOR MANUFACTURING NEOHEXENE

(75) Inventors: Jean Marie Basset, Caluire (FR); Francois Stoffelbach, Lyons (FR); Mostafa Taoufik, Villeurbanne (FR); Jean Thivolle-Cazat, Fontaines sur Saone (FR)

(73) Assignee: BP Oil International Limited, Middlesex (GB)

( * ) Notice: Subject to any disclaimer, the term of this patent is extended or adjusted under 35 U.S.C. 154(b) by 21 days.

(21) Appl. No.: 12/448,216

(22) PCT Filed: Dec. 11, 2007

(86) PCT No.: PCT/GB2007/004753
§ 371 (c)(1),
(2), (4) Date: Jun. 12, 2009

(87) PCT Pub. No.: WO2008/071949
PCT Pub. Date: Jun. 19, 2008

(65) Prior Publication Data
US 2010/0030003 A1    Feb. 4, 2010

(30) Foreign Application Priority Data
Dec. 14, 2006  (EP) .................................. 06256359

(51) Int. Cl.
*C07C 6/04* (2006.01)
(52) U.S. Cl. ...................... 585/646; 585/500; 585/643
(58) Field of Classification Search ............... 585/500, 585/643, 646
See application file for complete search history.

(56) References Cited

U.S. PATENT DOCUMENTS

| 3,660,516 | A | * | 5/1972 | Crain et al. | 585/316 |
|---|---|---|---|---|---|
| 3,729,524 | A | * | 4/1973 | Reusser | 585/329 |
| 3,767,565 | A | * | 10/1973 | Banks | 208/93 |
| 4,331,559 | A | * | 5/1982 | Banasiak | 502/154 |
| 4,542,249 | A | * | 9/1985 | Reusser | 585/329 |
| 4,559,320 | A | * | 12/1985 | Reusser | 502/251 |
| 5,905,055 | A | * | 5/1999 | Verdonck et al. | 502/311 |
| 6,583,329 | B1 | * | 6/2003 | Podrebarac | 585/646 |
| 7,041,861 | B2 |  | 5/2006 | Podrebarac |  |

FOREIGN PATENT DOCUMENTS

| WO | WO 2006/013263 |  | 2/2006 |
| WO | WO 2006093058 | A1 * | 9/2006 |

OTHER PUBLICATIONS

DIPPR Data (Design Institute for Physical Properties), AIChE, 2005-2011, on-line version available at www.knovel.com.*
Pearson, "Alumina" in Kirk-Othmer Encyclopedia of Chemical Technology, John Wiley, 2003, available on line Jan. 17, 2003.*
Machine Translation of WO2006-093058.*
Lide, CRC Handbook of Chemistry and Physics, 91st Edition, 2011 Internet Version, D. R. Lide, ed.*
Atlas, et al., Chem. Abs. 1991:474932, "Synthesis of Neohexene and 2,3-dimethylbutenes from Isobutylene," Doklady—Akademiya Nauk Azerbaidzhanskoi SSR (1989), 45(9), 41-5.*
International Search Report for PCT/GB2007/004753, mailed Mar. 18, 2008.
Written Opinion of the International Searching Authority for PCT/GB2007/004753, mailed Mar. 18, 2008.

* cited by examiner

*Primary Examiner* — In Suk Bullock
*Assistant Examiner* — Bradley Etherton
(74) *Attorney, Agent, or Firm* — Nixon & Vanderhye

(57) ABSTRACT

The present invention relates to a process for manufacturing neohexene, comprising contacting isobutene with a supported catalyst comprising a tungsten compound chosen from tungsten hydrides, organometallic tungsten compounds and organometallic tungsten hydrides, and a support comprising an oxide of aluminum, so as to form a reaction mixture comprising neohexene, and preferably separating neohexene from the reaction mixture, so as to isolate it. The contacting leads to the direct production of neohexene, in particular in a single (reaction) stage and with a high molar selectivity for neohexene. The contacting can be performed at a temperature of 50 to 600° C., under a total absolute pressure of 0.01 to 100 MPa.

23 Claims, No Drawings

PROCESS FOR MANUFACTURING NEOHEXENE

This application is the U.S. national phase of International Application No. PCT/GB2007/004753 filed 11 Dec. 2007, which designated the U.S. and claims priority to Europe Application No. 06256359.8 filed 14 Dec. 2006, the entire contents of each of which are hereby incorporated by reference.

The present invention relates to a process for manufacturing neohexene. Neohexene, also called 3,3-dimethyl-1-butene, belongs to the family of the branched α-olefins (or alpha-olefins), that is to say olefins having an olefinic double bond situated on the first carbon atom and possessing one or more hydrocarbon branchings. According to the definition of the prefix "neo", neohexene possesses a particular terminal branching corresponding to the radical —C(CH$_3$)$_3$.

Neohexene conforms to the general formula (I):

$$CH_2=CH-C(CH_3)_3 \qquad (1)$$

Neohexene is known to possess a very high octane number, for example an RON (Research Octane Number) of 111.7, an MON (Motor Octane Number) of 93.3 (according to Internal Combustion Engines and Air Pollution, 1973, by E. F. Obert), and a relatively low vapour pressure of 48 kPa at 20° C. For this reason, neohexene is an attractive product in the oil industry, and can in particular be used as an additive in gasolines for the motor car. In addition, neohexene can be used as an important intermediate product in the synthesis of perfume based on synthetic musk, in particular under the title "Tonalide"®. Neohexene can also be used as a fungicidal agent, in particular under the title "Terbinafine"®. It would therefore be highly desirable to develop a process for manufacturing neohexene which is simple, direct and inexpensive.

American U.S. Pat. No. 7,041,861 B2 discloses processes for the metathesis of olefins and in particular a process for manufacturing neohexene comprising two stages. First of all, a first stage comprises the metathesis of isobutene with itself, so as to produce a mixture of ethylene, 2,3-dimethyl-2-butene (or tetramethylethylene), C$_8$ oligomers of isobutene, in particular diisobutene (or 2-methyl-4.4-dimethyl-2-pentene), and heavy C$_{12}$ oligomers of isobutene. After having separated the components of said mixture and more particularly removed the heavy oligomers, a second stage of metathesis between the diisobutene and the ethylene is performed, so as to produce neohexene. It is stated more generally that in the processes for the metathesis of olefins, it is possible to use metathesis catalysts chosen from supported oxides of cobalt, molybdenum or rhenium or mixtures of supported oxides of cobalt and molybdenum, with a support either of silica or of alumina.

It is stated more particularly that in the first stage of the manufacture of neohexene, as illustrated in FIG. 5, a catalyst based on acidic cation resin is used. It appears that the process for manufacturing neohexene is complex, since it comprises two distinct reaction stages and an intermediate removal of heavy oligomers.

International Patent Application WO 98/02244 discloses a process for the metathesis of alkanes in the presence of a metal catalyst comprising a metal hydride grafted and dispersed onto a solid oxide, such as a hydride of tantalum or of tungsten grafted onto a silica. However, said process relates to the manufacture of alkanes and not of olefins, and even less of branched α-olefins such as neohexene.

International Patent Application WO 2004/089541 discloses a supported alkane metathesis catalyst comprising a tungsten hydride and a support based on aluminium oxide. It is shown that said catalyst can be used in reactions for the metathesis of hydro-carbons and can exhibit in said conditions a very high selectivity in the production of normal hydrocarbons (i.e. unbranched hydrocarbons). In addition, a use of said catalyst for manufacturing an olefin is neither envisaged nor suggested, and even less a branched α-olefin, in particular neohexene.

American U.S. Pat. No. 6,878,660 B2 discloses a catalyst containing an active rhenium compound having at least one carbene group, fixed to a solid support. The catalyst can be used in olefin metathesis reactions, in particular in self-metathesis reactions, in which an olefin is converted into two olefins of different molar mass, for example propylene converted into ethylene and 2-butene. It can also be used in co-metathesis (or cross-metathesis) reactions, in which two different olefins are converted into two other olefins, for example propylene and 1-butene converted into ethylene and 2-pentene. Examples of the use of the rhenium catalyst supported on silica in various metathesis reactions are shown: a metathesis of 3-heptene converted into 3-hexene and 4-octene, a metathesis of propylene converted into 2-butene and ethylene, and a co-metathesis of propylene and isobutene in which a conversion into ethylene, 2-methyl-2-butene and 2-butene has been observed. The manufacturing by this process of an α-olefin is neither envisaged nor suggested, and even less a branched α-olefin, in particular neohexene.

International Patent Application WO 2006/013251 discloses a process for converting ethylene into propylene, in which the ethylene is reacted with a supported metal compound containing a tungsten hydride grafted onto a support based on aluminium oxide. According to the patent application, it is assumed that the reaction involves at least in part a first stage of dimerisation of the ethylene into butene, then a reaction between the ethylene and the butene leading to propylene. Said process is very far from envisaging the manufacture of a branched α-olefin, in particular neohexene.

International Patent Application WO 2006/013263 discloses a process for the metathesis of compounds containing an olefinic double bond, in particular of olefins, in the presence of a catalyst based on tungsten hydride and supported on an aluminium oxide. The olefins used in the process are described in a very general way, namely olefins having a linear or branched hydrocarbon chain containing an olefinic double bond of the type Csp$^2$=Csp$^2$ (olefinic structure) and with the formula R$_1$R$_2$C=CR$_3$R$_4$, in which the substituents R$_i$ (i=1 to 4) are identical or different and can be of the type: hydrogen, methyl, ethyl, propyl or isopropyl, butyl, sec-butyl or isobutyl, pentyl, sec-pentyl, isopentyl or neopentyl.

In particular, various examples of metathesis are shown: a metathesis of propylene converted into ethylene and butenes, and a co-metathesis of ethylene and 2-butene converted into propylene. The use of said catalyst in a reaction for the metathesis of isobutene is neither envisaged nor suggested, and even less with the aim of manufacturing a branched α-olefin, in particular with a branching of the "neo" type, such as neohexene.

It was found in an unexpected manner that, contrary to the teaching of American U.S. Pat. No. 7,041,861 B2, it is now possible to convert isobutene directly into neohexene by a simple process comprising more particularly a single (reaction) stage. It was also found in a surprising manner that, contrary to the teaching of American U.S. Pat. No. 6,878,660 B2 and International Patent Application WO 2006/013263, it is now possible to convert an olefin such as isobutene into an α-olefin, more particularly a branched α-olefin, in particular with a branching of the "neo" type, such as neohexene. Thus, for the first time, due to a catalytic reaction of the isobutene performed in the presence of a specific tungsten catalyst supported on a solid based on aluminium oxide, it is possible to manufacture directly, in particular in a single (reaction) stage, and with a high selectivity, a branched α-olefin such as neohexene.

The present invention relates to a process for manufacturing neohexene, characterised in that isobutene is contacted with a supported metal catalyst comprising a tungsten compound chosen from tungsten hydrides, organometallic tungsten compounds and organometallic tungsten hydrides, and a support comprising an aluminium oxide, so as to form a reaction mixture comprising neohexene, and in that the neohexene is preferably separated and isolated from the reaction mixture.

In the process, it is preferred to use the isobutene alone or substantially alone, that is to say the isobutene optionally mixed with other hydrocarbon(s), in particular other olefin(s), so that the isobutene represents in said mixture more than 80%, preferably more than 90%, in particular more than 95% of the total olefins in moles.

In a highly advantageous manner, the process can be carried out in a single (reaction) stage which comprises in particular the contacting of the isobutene with the catalyst, so as to form a reaction mixture comprising neohexene, and preferably to separate and to isolate neohexene from said mixture.

It is observed that according to the process of the invention, the contacting of the isobutene with the catalyst leads directly to the formation of a reaction mixture comprising neohexene and generally other compounds, such as 2,3-dimethyl-2-butene (or tetramethylethylene), 2,3-dimethyl-1-butene and ethylene, and optionally diisobutene (or 2-methyl-4,4-dimethyl-2-pentene) and unreacted isobutene. The molar proportion of neohexene in the reaction mixture thus obtained is generally at least 5%, preferably at least 15%, and often can vary from 5 to 35% and sometimes up to about 50%. In addition, the reaction mixture can comprise 2,3-dimethyl-1-butene from 30 to 40%, 2,3-dimethyl-2-butene from 7 to 10%, ethylene from 10 to 30% and diisobutene from 5 to 10% (percentages expressed in moles). It is found that the reaction mixture generally comprises no heavy oligomers of isobutene, in particular $C_{12}$ or more, or at least in concentrations so low that they cannot be detected. This represents an obvious advantage of the process, since it is thus possible to avoid a specific stage of separation of said oligomers.

The neohexene can be produced with a relatively-high molar selectivity, in particular equal to or more than 5%, preferably equal to or more than 15% or even higher than 20%. By molar selectivity in neohexene (expressed in %) it is meant generally the ratio (multiplied by 100) of the number of moles of neohexene produced to the total number of moles of all the hydrocarbons produced, which ratio can be written according to the following equation (2):

Molar selectivity$_{(neohexene)}$=100×(number of moles of neohexene produced/total number of moles of all hydrocarbons produced)  (2)

In the same way and in a more general manner, a molar selectivity in an olefin (O) (expressed in %) produced during the contacting can also be defined as being the ratio (multiplied by 100) of the number of moles of said olefin (O) produced to the total number of moles of all the hydrocarbons produced, which ratio can be written according to the following equation (3):

Molar selectivity$_{(olefin\ (O))}$=100×(number of moles of olefin (O) produced/total number of moles of all hydrocarbons produced)  (3)

The contacting of the isobutene is performed with a specific tungsten catalyst supported on a solid comprising an aluminium oxide. It was found that, due precisely to said catalyst, it is now possible to convert the isobutene directly to neohexene, in particular in a single (reaction) stage and with a relatively high selectivity, as described above. The catalyst can, preferably, comprise a support comprising an aluminium oxide onto which is grafted (or fixed) the tungsten compound, as described above. Thus, a tungsten atom of the catalyst can be bonded to at least one oxygen atom of the aluminium oxide, in particular by a single tungsten-oxygen bond (W—OAl). The tungsten atom can be, in addition, bonded to at least one hydrogen atom of the tungsten hydrides or the organo-tungsten hydrides, in particular by a single tungsten-hydrogen bond (W—H), and/or to at least one carbon atom of the organo-tungsten compounds or the organo-tungsten hydrides, in particular by a single, double or triple tungsten-carbon bond.

The support of the catalyst can be any solid support comprising an aluminium oxide, and in particular where the aluminium oxide is directly accessible at the surface of the support. The support is chosen, preferably, from homogeneous aluminium oxide supports having in particular a homogeneous composition throughout their structure. It can also be chosen from heterogeneous aluminium oxide supports, in particular supports in which the aluminium oxide is in the major component, preferably dispersed at the surface of the support. Thus, for example, the aluminium oxide can be dispersed, supported on or grafted onto, a solid support that can itself be a support chosen from metallic or refractory oxides, sulfides, carbides, nitrides and salts, and from carbon, metals, open or closed mesoporous structures MCM21 and MCM22, organic/inorganic hybrid materials and molecular sieves, in particular chosen from silica and metallic or refractory oxides.

The support can have a specific surface area (B.E.T) measured according to the standard ISO 9277 (1995) which is chosen in a range of from 0.1 to 5000 $m^2/g$, preferably from 1 to 3000 $m^2/g$, particularly from 1 to 1000 m2/g, the largest specific surface area being preferred when diffusion does not control the reaction.

More particularly, the support can be chosen from simple aluminium oxides, mixed aluminium oxides and aluminium oxides modified more particularly by one or more elements of Groups 13 to 17, preferably of Groups 15 to 17 of the Periodic Table of the Elements. In the present description, there is called the Periodic Table of the Elements that presented by IUPAC in 1991 and published, for example, by CRC Press, Inc., USA in "CRC Handbook of Chemistry and Physics" 76th edition (1995-1996), by David R. Lide.

The support can preferably be chosen from simple aluminium oxides. By simple aluminium oxide, also called simple alumina, is understood generally an aluminium oxide substantially free of any other oxide, more particularly containing less than 2 wt % of one or more other oxides, that are generally present in the form of impurities. If the aluminium oxide contains 2 wt % or more of one or more other oxides, it is generally agreed to regard the oxide as a mixed aluminium oxide, generally an aluminium oxide combined with at least one other oxide. A simple aluminium oxide can be chosen in particular from porous aluminas, semi-porous aluminas, non-porous aluminas and mesoporous aluminas.

Thus, the support can be a porous alumina, often called "activated alumina" or "transition alumina". The porous alumina corresponds generally to various types of partially hydroxylated aluminium oxide ($Al_2O_3$). It is generally obtained by an activation treatment comprising more particularly a thermal (or dehydration) treatment of a precursor chosen for example from aluminium hydroxides such as aluminium trihydroxides, hydroxides of the aluminium oxide (or hydrates of the aluminium oxide) and gelatinous aluminium hydroxides (or alumina gels). The activation treatment makes it possible to remove the water contained in the precursor, and also a part of the hydroxyl groups, and to allow some residual hydroxyl groups and a porous structure to remain. Eventually, the porous structure may be avoided, when a flame alumina is used, and in this case the pre-treatment also removes the hydroxyl groups. The surface of the porous alumina comprises generally a complex mixture of atoms of aluminium and of oxygen, and also of hydroxyl ions that can combine according to specific crystalline forms and present acidic and basic sites. The different crystalline forms depend generally on the choice of the precursor and the conditions of the activation treatment, for example the use of a current of air or of another gas such as an inert gas, the pressure or the temperature, which can be chosen in a range of from 100 to 1000° C., preferably from 150 to 1000° C. The support can be a porous alumina chosen more particularly from a $\gamma$-alumina (gamma alumina), a $\eta$-alumina (eta alumina), a $\delta$-alumina (delta alumina), a $\theta$-alumina (theta alumina), a $\kappa$-alumina (kappa alumina), a $\rho$-alumina (rho alumina), a $\alpha$-alumina (alpha-alumina) and a $\chi$-alumina (ksi- or chi alumina). It is preferred to choose the support from a $\gamma$-alumina and a $\eta$-alumina. The porous alumina can have a specific surface area (B.E.T.) chosen in a range of from 100 to 1000 $m^2/g$, preferably from 100 to 5000 $m^2/g$, more particularly from 200 to 3000 $m^2/g$, in particular from 300 to 1000 $m^2/g$. It can also possess a specific pore volume equal to or less than 1.5 $cm^3/g$, preferably equal to or less than 1.2 $cm^3/g$, more particularly equal to or less than 1.0 $cm^3/g$.

The support can also be a semi-porous alumina. The latter is generally obtained by an activation treatment as described above, more particularly at a temperature ranging from 600 to 1000° C. It can generally comprise a mixture of a porous alumina, such as one of those described above, with a non-porous alumina chosen in particular from an $\alpha$-alumina (alpha alumina) and a $\gamma$-alumina (gamma alumina), in ratios by weight between porous alumina and non-porous alumina that can range from 10/90 to 90/10, in particular from 20/80 to 80/20.

The support can also be a non-porous alumina, known generally under the term "calcined alumina" or "flame alumina". The non-porous alumina can be an $\alpha$-alumina (alpha alumina) or a $\gamma$-alumina (gamma alumina). The $\alpha$-alumina exists in the natural state under the name "corundum" and can contain impurities such as other oxides at the rate of less than 2 wt %, preferably of less than 1 wt % or less. It can also be synthesised, generally by a thermal, oxidation or calcination treatment of a precursor chosen more particularly from aluminium alkyls, aluminium salts, hydroxides of the aluminium oxide, aluminium trioxides and aluminium oxides, in particular at a temperature of more than 1000° C., preferably equal to or more than 1100° C. The non-porous aluminas can have a specific surface area (B.E.T.) chosen in a range of from 0.1 to 300 $m^2/g$, preferably from 0.5 to 300 $m^2/g$, more particularly from 0.5 to 250 $m^2/g$.

The support can also be a mesoporous alumina having more particularly a specific surface area (B.E.T.) chosen in a range of from 100 to 800 $m^2/g$, and having in particular pores with a width chosen in a range of from 2 nm to 0.05 µm.

The support can be chosen from mixed aluminium oxides. By mixed aluminium oxide is meant generally an aluminium oxide combined with at least one other oxide in a proportion by weight that can be chosen in a range of from 2 to less than 80%, preferably from 2 to less than 50%, in particular from 2 to less than 40% or even from 2 to less than 30%. The other oxide or oxides can be oxides of the elements (M) chosen from the metals of Groups 1 to 13 and from the elements of Group 14, with the exception of carbon, of the Periodic Table of the Elements. The element (M) is in particular chosen from alkaline metals, alkaline-earth metals, transition metals, lanthanides and actinides, preferably chosen from silicon, boron, gallium, germanium, titanium, zirconium, cerium, vanadium, niobium, tantalum, chromium, molybdenum and tungsten. More particularly, the mixed aluminium oxides can be chosen from anhydrous aluminates, spinels, silica-aluminas and aluminosilicates.

The support can also be chosen from aluminium oxides modified more particularly by one or more elements of Groups 13 to 17, preferably of Groups 15 to 17, of the Periodic Table of the Elements. Aluminium oxides modified by boron, phosphorus, sulfur, fluorine and/or chlorine can be chosen. The support can be chosen in particular from the super-acids of alumina, or from boron, borated, boric, phosphorus, phosphated, pyrophosphated, phosphoric, orthophosphoric, phosphorous, orthophosphorous, sulfur, sulfated, sulfurised, sulfuric, sulfurous, chlorine, chlorinated, fluorine or fluorinated oxides of aluminium, preferably from chlorinated oxides of aluminium. Phosphated oxides of aluminium either amorphous or crystalline or else in molecular sieve forms may also be chosen as catalyst supports.

The support generally is in the form of particles that can have any shape and any size. The particles can have a mean size chosen in a very wide range of from 10 nm to 10 mm, preferably from 20 nm to 5 mm. They can also have a spherical, spheroidal, hemispherical, hemispheroidal, cylindrical or cubic shape, or a ring, pellet, disc or granule shape, or else a shape of packing materials such as those used in distillation column reactors, as described in American U.S. Pat. No. 4,242,530.

The catalyst comprises a tungsten compound chosen from tungsten hydrides, organometallic tungsten compounds and organometallic tungsten hydrides. The tungsten present in the catalyst can have a degree of oxidation of from 2 to 6, preferably from 4 to 6.

The tungsten compound can be first of all chosen from tungsten hydrides in which the tungsten atom can be bonded to one or more hydrogen atoms, in particular by a single (W—H) bond. The number of hydrogen atoms bonded per tungsten atom can be chosen from 1 to 5, preferably from 1 to 4, more particularly from 1 to 3. It depends on the degree of oxidation of the tungsten. When the tungsten compound is fixed or grafted onto the support, it can also depend on the number of bonds existing between the tungsten and the support, more particularly between the tungsten atom and one or more oxygen atoms of the aluminium oxide.

The tungsten compound can also be chosen from organometallic tungsten compounds. By organometallic tungsten compound is meant generally an organo-metallic tungsten compound in which the tungsten atom is bonded to at least one carbon atom of a hydrocarbon radical, in particular by a single, double or triple bond. The number of hydrocarbon radicals bonded per tungsten atom can be from 1 to 5, preferably from 1 to 4, in particular from 1 to 3. It depends on the degree of oxidation of the tungsten, and optionally on the number of bonds existing between the tungsten and the support, when the tungsten compound is more particularly fixed or grafted onto the support. The organometallic tungsten compound can comprise one or more hydrocarbon radicals (R), either identical or different, linear or branched, saturated or unsaturated, in particular comprising from 1 to 20, preferably from 1 to 14 carbon atoms. The hydrocarbon radical (R) can be monovalent, divalent or trivalent. They can be chosen from linear or branched, aliphatic, alicyclic or aromatic, saturated or unsaturated hydrocarbon radicals, in particular from alkyl (monovalent) radicals, more particularly from $C_1$ to $C_{10}$, for example the radicals methyl, ethyl, n-propyl, isopropyl, n-butyl, isobutyl, neopentyl or allyl, from alkylidene (divalent) radicals, more particularly from $C_1$ to $C_{10}$, for example the radicals methylidene, ethylidene, n-propylidene, isopropylidene, n-butylidene, isobutylidene, neopentylidene or allylidene, from alkylidyne (trivalent) radicals, more particularly from $C_1$ to $C_{10}$, for example the radicals ethylidyne, propylidyne, butylidyne, neopentylidyne or allylidyne, from aryl (monovalent) radicals, more particularly from $C_6$ to $C_{12}$, for example the radical phenyl, from aralkyl (monovalent) radicals, more particularly from $C_7$ to $C_{14}$, aralkylidene (divalent) radicals, more particularly from $C_7$ to $C_{14}$, and aralkylidyne (trivalent) radicals, more particularly from $C_7$ to $C_{14}$. The hydrocarbon radicals can also comprise organic functions, preferably chosen from ketones, esters and amines.

The tungsten compound can also be chosen from organometallic tungsten hydrides. By organometallic tungsten hydride is meant generally a tungsten hydride in which the tungsten atom already bonded to at least one hydrogen atom is also bonded to at least one carbon atom of a hydrocarbon radical, more particularly a hydrocarbon radical (R) as described above. The organometallic tungsten hydride can comprise one or more hydrocarbon radicals (R), either identical or different, linear or branched, saturated or unsaturated, in particular comprising from 1 to 20, preferably from 1 to 14 carbon atoms. The hydrocarbon radicals (R) can be monovalent, divalent or trivalent, and can be chosen from those described above. The total number of atoms of hydrogen and of hydrocarbon radicals bonded per tungsten atom can be from 2 to 5, preferably from 2 to 4, more particularly from 2 to 3. The respective numbers of hydrogen atoms and of carbon atoms bonded per tungsten atom can be respectively from 1 to 4 and from 4 to 1, preferably from 1 to 3 and from 3 to 1, more particularly from 1 to 2 and from 2 to 1, on condition that the respective total numbers of hydrogen and carbon atoms bonded per tungsten atom that were mentioned above are respected. It is preferred to use a catalyst having a tungsten compound chosen in particular from organometallic tungsten hydrides.

The catalyst is a tungsten compound as described above, which also can comprise one or more ligands, such as "ancillary" ligands, preferably comprising at least one oxygen atom and/or at least one nitrogen atom. The ligands can be identical or different, and be preferably chosen from oxo, alkoxo, aryloxo, aralkyloxo, nitrido, imido and amido ligands. There is meant generally by oxo, alkoxo, aryloxo, aralkyloxo, nitrido, imido and amido ligand respectively:
  a divalent oxo radical with the general formula: =O,
  a monovalent alkoxo, aryloxo or aralkyloxo radical with the general formula: —OR',
  a trivalent nitrido radical with the general formula: ≡N,
  a divalent imido radical with the general formula: =NR", and
  a monovalent amido radical with the general formula: —NR¹R² (a description of these general formulae will be given later). The presence of oxo, alkoxo, aryloxo, aralkyloxo, nitrido, imido and/or amido ligands in the tungsten compounds can influence favourably the behaviour of the catalyst in the process for manufacturing neohexene.

By tungsten compound comprising at least one oxo ligand is meant generally one of the tungsten compounds mentioned above, in which the tungsten atom already bonded to at least one hydrogen atom and/or to at least one hydrocarbon radical (R) is in addition bonded to at least one oxo ligand with the formula (4):

=O  (4)

in which formula O represents an oxygen atom. Thus, a tungsten hydride, an organometallic tungsten compound or an organometallic tungsten hydride such as those described and comprising at least one oxo ligand can conform to the formulae (5), (6) and (7) respectively:

H—W=O  (5)

R—W=O  (6)

H—W=O
    |
    R  (7)

in which formulae W represents a tungsten atom, O represents an oxygen atom, H represents a hydrogen atom and R represents the hydrocarbon radical (R) described above, it being understood that the tungsten atom can also be bonded, preferably, to the support, more particularly by at least one single bond (not shown in said formulae) bonding the tungsten atom to an oxygen atom of the aluminium oxide (W—OAl). Thus, it can be considered that the tungsten compound can be an oxo-tungsten hydride according to formula (5), a hydrocarbyl oxo-tungsten compound according to formula (6) or a hydrocarbyl oxo-tungsten hydride according to formula (7).

The number of oxo ligands per tungsten atom can be equal to 1, 2 or 3, preferably equal to 1 or 2. It depends on the degree of oxidation of the tungsten, on the number of (W—H) and/or (W—R) bonds existing respectively between the tungsten atom and the hydrogen atom(s) and/or the hydrocarbon radical(s) (R), and optionally on the number of bonds between the tungsten and the support. Thus, a tungsten compound comprising one or more oxo ligands per tungsten atom can be in particular a mono-, bis- or tris(oxo)-tungsten compound, preferably a mono- or bis(oxo)-tungsten compound.

By tungsten compound comprising at least one alkoxo, aryloxo or aralkyloxo ligand is meant generally one of the tungsten compounds mentioned above, in which the tungsten atom already bonded to at least one hydrogen atom and/or to at least one hydrocarbon radical (R) is in addition bonded to at least one alkoxo, aryloxo or aralkyloxo ligand of the formula (8):

—OR'  (8)

in which formula O represents an oxygen atom and R' represents a hydrogen atom or a monovalent hydrocarbon radical selected respectively from alkyl, aryl and aralkyl radicals. More particularly, the monovalent hydrocarbon radical (R') can be linear or branched, saturated or unsaturated, comprising from 1 to 20, preferably from 1 to 14 carbon atoms, and be chosen in particular from alkyl radicals, more particularly from $C_1$ to $C_{10}$, aralkyl radicals, more particularly from $C_7$ to $C_{14}$, and aryl radicals, more particularly from $C_6$ to $C_{12}$. Thus, a tungsten hydride, an organometallic tungsten compound or an organometallic tungsten hydride such as those described above and comprising at least one alkoxo, aryloxo or aralkyloxo ligand can conform to the formulae (9), (10) and (11) respectively:

$$H\!-\!W\!-\!OR' \tag{9}$$

$$R\!-\!W\!-\!OR' \tag{10}$$

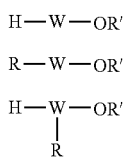
(11)

in which formulae W represents a tungsten atom, O represents an oxygen atom, H represents a hydrogen atom, R represents the hydrocarbon radical (R) described above, and R' represents a hydrogen atom or the monovalent hydrocarbon radical described previously, in the knowledge that the tungsten atom can also be bonded, preferably, to the support, more particularly by at least one single bond (not shown in said formulae) linking the tungsten atom to an oxygen atom of the aluminium oxide (W—OAl). Thus, it can be considered that the tungsten compound can be an alkoxo/aryloxo/aralkyloxo-tungsten hydride according to formula (9), a hydrocarbyl alkoxo/aryloxo/aralkyloxo-tungsten compound according to formula (10) or a hydrocarbyl alkoxo/aryloxo/aralkyloxo-tungsten hydride according to formula (11).

The number of alkoxo, aryloxo or aralkyloxo ligands per tungsten atom can vary from 1 to 4, preferably from 1 to 3, and more particularly equal to 1 or 2. It depends on the degree of oxidation of the tungsten, on the number of (W—H) and/or (W—R) bonds existing respectively between the tungsten atom and the hydrogen atom(s) and/or the hydrocarbon radical(s) (R), and optionally on the number of bonds between the tungsten and the support. Thus, a tungsten compound comprising one or more alkoxo/aryloxo/aralkyloxo ligands per tungsten atom can be in particular a mono-, bis- or tris(alkoxo/aryloxo/aralkyloxo)-tungsten compound, preferably a mon- or bis(alkoxo/aryloxo/aralkyloxo)-tungsten compound.

By tungsten compound comprising at least one nitrido ligand is meant generally one of the tungsten compounds mentioned above, in which the tungsten atom already bonded to at least one hydrogen atom and/or to at least one hydrocarbon radical (R) is in addition bonded to at least one nitrido ligand of the formula (12):

$$\equiv\!N \tag{12}$$

in which formula N represents a nitrogen atom. Thus, A tungsten hydride, an organometallic tungsten compound or an organometallic tungsten hydride such as those described above and comprising at least one nitrido ligand can conform to the formulae (13), (14) and (15) respectively:

$$H\!-\!W\!\equiv\!N \tag{13}$$

$$R\!-\!W\!\equiv\!N \tag{14}$$

(15)

in which formulae W represents a tungsten atom, N represents a nitrogen atom, H represents a hydrogen atom, and R represents the hydrocarbon radical (R) described above, in the knowledge that the tungsten atom can also be bonded, preferably, to the support, more particularly by at least one single bond (not shown in said formulae) linking the tungsten atom to an oxygen atom of the aluminium oxide (W—OAl). Thus, it can be considered that the tungsten compound can be a nitrido-tungsten hydride according to formula (13), a hydrocarbyl nitrido-tungsten compound according to formula (14), or a hydrocarbyl nitrido-tungsten hydride according to formula (15).

The number of nitrido ligands per tungsten atom can be equal to 1 or 2, preferably equal to 1. It depends on the degree of oxidation of the tungsten, on the number (W—H) and/or (W—R) bonds existing respectively between the tungsten atom and the hydrogen atom(s) and/or the hydrocarbon radical(s) (R), and optionally on the number of bonds between the tungsten and the support. Thus, the tungsten compound comprising one or two nitrido ligands per tungsten atom can be in particular a mono- or bis(nitrido)-tungsten compound, preferably a mono(nitrido)-tungsten compound.

By tungsten compound comprising at least one imido ligand is meant generally one of the tungsten compounds mentioned above, in which the tungsten atom already bonded to at least one hydrogen atom and/or to at least one hydrocarbon radical (R) is in addition bonded to at least one imido ligand of the formula (16):

$$=\!NR'' \tag{16}$$

in which formula N represents a nitrogen atom and R" represents a hydrogen atom or a monovalent hydrocarbon radical. The monovalent hydrocarbon radical (R") can be linear or branched, saturated or unsaturated, comprising from 1 to 20, preferably 1 to 14 carbon atoms, and be chosen in particular from alkyl radicals, more particularly from $C_1$ to $C_{10}$, aralkyl radicals, more particularly from $C_7$ to $C_{14}$, and aryl radicals, more particularly from $C_6$ to $C_{12}$. Thus, a tungsten hydride, an organometallic tungsten compound or an organometallic tungsten hydride such as those described above and comprising at least one imido ligand can conform to the formulae (17), (18) and (19) respectively:

$$H\!-\!W\!=\!NR'' \tag{17}$$

$$R\!-\!W\!=\!NR'' \tag{18}$$

(19)

in which formulae W represents a tungsten atom, N represents a nitrogen atom, H represents a hydrogen atom, R represents the hydrocarbon radical (R) described above and R" represents a hydrogen atom or the monovalent hydrocarbon radical described above, in the knowledge that the tungsten atom can also be bonded, preferably, to the support, more particularly by at least one single bond (not shown in said formulae) linking the tungsten atom to an oxygen atom of the aluminium oxide (W—OAl). Thus, it can be considered that the tungsten compound can be an imido-tungsten hydride according to formula (17), a hydrocarbyl imido-tungsten compound according to formula (18) or a hydrocarbyl imido-tungsten hydride according to formula (19).

The number of imido ligands per tungsten atom can be equal to 1, 2 or 3, preferably equal to 1 or 2. It depends on the degree of oxidation of the tungsten, on the number of (W—H) and/or (W—R) bonds existing respectively between the tungsten atom and the hydrogen atom(s) and/or the hydrocarbon radical(s) (R), and optionally on the number of bonds between the tungsten and the support. Thus, a tungsten compound comprising one or more imido ligands per tungsten atom can be in particular a mono-, bis- or tris(imido)-tungsten compound, preferably a mono- or bis(imido)-tungsten compound.

By tungsten compound comprising at least one amido ligand is meant generally one of the tungsten compounds mentioned above, in which the tungsten atom already bonded to at least one hydrogen atom and/or to at least one hydrocarbon radical (R) is in addition bonded to at least one amido ligand of the formula (20):

$$—NR^1R^2 \quad (20)$$

in which formula N represents a nitrogen atom, and $R^1$ and $R^2$, being identical or different, represent a hydrogen atom or a monovalent hydrocarbon radical. The monovalent hydrocarbon radicals ($R^1$) and ($R^2$) can be linear or branched, saturated or unsaturated, comprising from 1 to 20, preferably 1 to 14 carbon atoms, and be chosen in particular from alkyl radicals, more particularly from $C_1$ to $C_{10}$, aralkyl radicals, more particularly from $C_7$ to $C_{14}$, and aryl radicals, more particularly from $C_6$ to $C_{12}$. Thus, a tungsten hydride, an organometallic tungsten compound or an organometallic tungsten hydride such as those described above, comprising at least one amido ligand, can conform to the formulae (21), (22) and (23) respectively:

$$H—W—NR^1R^2 \quad (21)$$

$$R—W—NR^1R^2 \quad (22)$$

$$\begin{array}{c} H—W—NR^1R^2 \\ | \\ R \end{array} \quad (23)$$

in which formulae W represents a tungsten atom, H represents a hydrogen atom, N represents a nitrogen atom, R represents the hydrocarbon radical (R) described above and $R^1$ and $R^2$, being identical or different, represent a hydrogen atom or a monovalent hydrocarbon radical described above, in the knowledge that the tungsten atom can also be bonded, preferably, to the support, more particularly by at least one single bond (not shown in said formulae) linking the tungsten atom to an oxygen atom of the aluminium oxide (W—OAl). Thus, it can be considered that the tungsten compound can be an amido-tungsten hydride according to formula (21), a hydrocarbyl amido-tungsten compound according to formula (22) or a hydrocarbyl amido-tungsten hydride according to formula (23).

The number of amido ligands bonded per tungsten atom can vary from 1 to 4, preferably from 1 to 3, and more particularly equal to 1 or 2. It depends on the degree of oxidation of the tungsten, on the number of (W—H) and/or (W—R) bonds existing respectively between the tungsten atom and the hydrogen atom(s) and/or the hydrocarbon radical(s) (R), and optionally on the number of bonds between the tungsten and the support. Thus, a tungsten compound comprising one or more amido ligands per tungsten atom can be in particular a mono-, bis- or tris(amido)-tungsten compound, preferably a mono- or bis(amido)-tungsten compound.

The tungsten compound chosen from the tungsten hydrides, the organometallic tungsten compounds and the organometallic tungsten hydrides can comprise a plurality of, in particular 2 or 3, different ligands (or "ancillary" ligands) preferably comprising at least one oxygen atom and/or at least one nitrogen atom, chosen in particular from oxo, alkoxo, aryloxo, aralkyloxo, nitrido, imido and amido ligands such as those described above.

The catalyst comprising a tungsten compound chosen from the tungsten hydrides and the organometallic tungsten hydrides, can exhibit in infra-red spectroscopy one or more absorption bands characteristic of the (W—H) bond, bands whose frequency can vary according to the co-ordination sphere of the tungsten and can depend on the number of bonds of the tungsten with the support and optionally with the hydrocarbon radicals (R) described above and with other hydrogen atoms. Thus, for example, at least two absorption bands were found at 1903 and 1804 $cm^{-1}$, bands characteristic of the (W—H) bond considered in the environment of the (W—OAl) bonds linking the same tungsten atom to an oxygen atom itself linked to an aluminium atom of the support, more particularly of an α-alumina or a γ-alumina. The (W—H) bond in the catalyst can also be characterised by NMR of the proton under 500 MHz where the value of the chemical shift of the tungsten hydride ($\delta_{W—H}$) can vary and depends on the other ligands and preparation conditions. In some typical cases, it may be equal to 0.6 ppm (parts per million).

The catalyst used in the invention and the procedures for its preparation are, for example, described in International Patent Application WO 2004/089541.

Thus, for example, the preparation of the catalyst can comprise the following stages:
(1) a stage of calcination under air or under oxygen of the support based on aluminium oxide, for example an α-alumina or a γ-alumina, for a period of 1 to 24 hours, at a temperature preferably chosen in a range of from 200 to 1000° C., in particular from 300 to 700° C., the calcination stage being preferably followed by a dehydroxylation stage under an atmosphere of an inert gas such as nitrogen, argon or helium, or else under vacuum, for a period of 1 to 24 hours, and at a temperature preferably chosen in a range of from 200 to 1000° C., in particular from 300 to 700° C.,
(2) a stage of dispersion and grafting onto the support prepared beforehand of an organo-metallic tungsten precursor (Pr), in which the tungsten can be bonded to at least one hydrocarbon radical (R) and optionally to at least one "ancillary" ligand such as those described above, so as to form an organometallic tungsten compound grafted onto the support, and optionally
(3) a stage of hydrogenolysis of the compound prepared beforehand, so as to form a tungsten hydride or an organometallic tungsten hydride grafted onto the support.

The process for manufacturing neohexene comprises a contacting of the isobutene with the catalyst. The contacting can be performed in various ways, discontinuously or preferably continuously, in a reaction zone (Z). For example, the isobutene can be added to the catalyst, or the catalyst be added to the isobutene, or else the isobutene and the catalyst be simultaneously added into a reaction zone (Z).

The contacting can be performed at a temperature chosen in a range of from 50 to 600° C., preferably from 70 to 550° C., in particular from 100 to 500° C. It can also be performed under a total absolute pressure, chosen in a range of from 0.01 to 100 MPa, preferably from 0.1 to 50 MPa, in particular from 0.1 to 30 MPa.

It can also be performed in the presence of an inert agent, either liquid or gaseous, in particular of an inert gas chosen in particular from nitrogen, argon and helium. It can also be advantageously performed in the presence of hydrogen or of an agent forming "in situ" hydrogen, such as a cyclic hydrocarbon chosen in particular from cyclohexane, decahydronaphthalene and tetrahydronaphthalene. The hydrogen present during the contacting can in particular play the role of an agent of activation or regeneration of the catalyst. For example, the hydrogen can be used in the contacting with a hydrogen partial pressure chosen in a wide range of from 0.1 kPa to 10 MPa, preferably from 1 kPa to 1 MPa.

In addition, the contacting can be performed with quantities of isobutene and catalyst such that the molar ratio of the isobutene to the tungsten of the catalyst is chosen in a range of from 1 to $10^7$, preferably from 2 to $10^5$, in particular from 5 to $10^4$. It can also be performed in a reaction zone (Z) containing the catalyst and into which the isobutene is introduced preferably continuously, and in particular with a molar rate of introduction of isobutene per mole of tungsten of the catalyst and per minute which can be chosen in a wide range of, for example, from 0.1 to $10^5$, preferably from 1 to $10^5$, in particular from 5 to $10^5$.

The contacting can be performed in a gaseous phase, or in mixed gaseous/liquid phase, or in liquid phase, or else in supercritical phase, in a reaction zone (Z) adapted to the phase chosen. In particular, the contacting can be performed mainly in gaseous phase in a reaction zone (Z), in particular under a pressure equal to or more than atmospheric pressure and less than the condensation pressure of neohexene, 2,3-dimethyl-2-butene, 2,3-dimethyl-1-butene and diisobutene.

The contacting can also be performed in a mixed gaseous/liquid phase in a reaction zone (Z), under a pressure equal to or more than the condensation pressure of 2,3-dimethyl-2-butene and of 2,3-dimethyl-1-butene, and less than the condensation pressure of neohexene, so as to maintain neohexene, isobutene and ethylene mainly in gaseous phase, preferably to separate and to isolate at least the neohexene from the gaseous phase, and preferably to separate from said gaseous phase a liquid phase comprising in particular 2,3-dimethyl-2-butene, 2,3-dimethyl-1-butene and diisobutene.

The contacting can also be performed in a mixed gaseous/liquid phase in a reaction zone (Z), under a pressure equal to or more than the condensation pressure of neohexene and less than the condensation pressure of isobutene, so as to maintain isobutene and ethylene mainly in gaseous phase, to recover the neohexene mainly in the liquid phase with the 2,3-dimethyl-2-butene, 2,3-dimethyl-1-butene and the diiso-butene, and preferably to separate and to isolate at least the neohexene from said liquid phase.

The contacting can also be performed in a mixed gaseous/liquid phase in a reaction zone (Z), under a pressure equal to or more than the condensation pressure of isobutene and less than the condensation pressure of ethylene, so as to maintain ethylene mainly in the gaseous phase, while the rest of the reaction mixture is maintained mainly in the liquid phase.

The contacting in a mixed gaseous/liquid phase such as described above can be advantageously performed in a distillation column reactor, as described below or in American U.S. Pat. No. 4,242,530.

The contacting can also be performed in a liquid phase in a reaction zone (Z), in particular under a pressure equal to or more than the condensation pressure of ethylene.

The contacting can also be performed in a supercritical phase in a reaction zone (Z) in which the catalyst is in suspension in the isobutene, in particular at a temperature higher than the critical temperature of all the products involved and produced in the process, or under a pressure higher than the critical pressure of all the products involved and produced in the process.

It may be particularly advantageous to perform the contacting:
(i) by continuously introducing the isobutene into a reaction zone (Z) containing the catalyst, so as to form the reaction mixture preferably continuously, and
(ii) by continuously withdrawing out of said zone (Z) at least one part of the reaction mixture, so as to subject preferably continuously said part of the reaction mixture to one or more external and preferably continuous fractionation(s) outside the reaction zone (Z), and preferably to separate and to isolate one or more component(s) of the reaction mixture, in particular the neohexene, preferably continuously.

It may also be found to be particularly advantageous to perform the contacting:
(i) by continuously introducing the isobutene into a reaction zone (Z) containing the catalyst, so as to form the reaction mixture preferably continuously, under conditions such that one or more component(s) of said reaction mixture, in particular ethylene, isobutene and optionally neohexene, are essentially maintained in a gaseous phase, while the rest of the reaction mixture is essentially maintained in a liquid phase (i.e. under conditions leading to a mixed gaseous/liquid phase),
(ii) by continuously withdrawing out of said zone (Z) at least one part of the gaseous phase, so as to subject optionally said part of the gaseous phase to at least one external and preferably continuous fractionation, and preferably to separate and to isolate one or more component(s) of said part of the gaseous phase, in particular the neohexene, preferably continuously, and optionally to recycle at least one of said component(s) thus separated and isolated, in particular the isobutene, into the reaction zone (Z), preferably continuously, and
(iii) by continuously withdrawing out of said zone (Z) at least one part of the liquid phase, so as to subject optionally said part of the liquid phase to at least one external and preferably continuous fractionation, and preferably to separate and to isolate one or more component(s) of said part of the liquid phase, in particular the neohexene, preferably continuously, and optionally to recycle at least one of said component(s) thus separated and isolated, in particular the isobutene, into the reaction zone (Z), preferably continuously.

It may also be found to be particularly advantageous to perform the contacting:
(i) by continuously introducing the isobutene into a reaction zone (Z) containing the catalyst, so as to form the reaction mixture preferably continuously, under conditions such that at least two components of the reaction mixture, in particular ethylene, isobutene and optionally neohexene, are essentially maintained in a gaseous phase and are subjected to an internal and preferably continuous fractionation in a part of said reaction zone (Z), while the rest of the mixture is essentially maintained in a liquid phase (i.e. under conditions leading to a mixed gaseous/liquid phase),
(ii) by continuously withdrawing out of said reaction zone (Z) the component(s) of the gaseous phase thus fractioned, so as to isolate it (or them), in particular the neohexene, preferably continuously, and optionally to recycle it (or them), in particular the isobutene, into the reaction zone (Z), preferably continuously, and
(iii) by continuously withdrawing out of said reaction zone (Z) at least one part of the liquid phase, so as to subject optionally said part of the liquid phase to at least one external and preferably continuous fractionation, and preferably to separate and to isolate the component(s) of said part of the liquid phase, in particular the neohexene, preferably continuously.

In every case, the contacting can be performed in a reaction zone (Z) containing the catalyst. The catalyst is generally solid, in particular in the form of solid particles, for example in the form of a distillation packing or of a bed, through which a stream of gaseous or liquid isobutene passes, or in the form of solid particles which are maintained in suspension by the gaseous or liquid isobutene, or entrained in the form of a current with the gaseous or liquid isobutene.

The contacting can be performed in a reaction zone (Z) comprising a static reactor, a recycling reactor or a dynamic reactor. Thus, for example, the contacting can be performed in a static reactor containing fixed quantities of isobutene and catalyst introduced for a complete reaction cycle. The contacting can also be performed in a recycling reactor in which it is possible to recycle at least one of the components of the reaction mixture formed, preferably unreacted isobutene, which can be separated from the reaction mixture by a prior fractionation either inside or outside the reactor. The contacting can also be performed in a dynamic reactor in which a stream of gaseous or liquid isobutene passes into or through a bed comprising the catalyst.

In practice, the contacting can be performed in a reaction zone (Z) comprising a reactor chosen from tubular (or multi-tubular) reactors, distillation column reactors, slurry reactors, fluidised bed reactors, mechanically agitated bed reactors, fluidised and mechanically agitated bed reactors, fixed bed reactors and circulating bed reactors. The generally solid catalyst, in particular in particle form, can be arranged inside the tube(s) of a tubular (or multi-tubular) reactor. Thus, the isobutene introduced, preferably continuously, into the tube (s) can pass through it (or them) in the form of a stream and thus be contacted with the catalyst, so as to form the reaction mixture. The catalyst can also be arranged inside a distillation reactor, wherein the catalyst is preferably a component of a distillation system functioning as both a catalyst and a distillation packing, i.e. a packing for a distillation column having both a distillation function and a catalytic function: for example, rings, saddles, granulates, sheets, tubes, spirals, packed in bags, as described in American U.S. Pat. No. 4,242, 530. The catalyst can also form the bed of a fluidised and/or mechanically agitated bed reactor, of a fixed bed reactor, or of a circulating bed reactor. The catalyst can be used in one said reactors, optionally in mixture with at least one inert solid agent, preferably chosen from silicas, aluminas, silica-aluminas and aluminium silicates. The isobutene can be introduced into one of said reactors preferably continuously, and generally can pass or circulate preferably continuously in the form of a gaseous or liquid stream into the tube(s), or through the bed or the distillation packing of said reactors. In order to promote the development of the reaction towards an optimum production of neohexene, the process can be advantageously performed by withdrawing preferably continuously one or more component(s) of the reaction mixture, preferably the neohexene.

Preferably, the process also comprises separating the neohexene from the reaction mixture, so as to isolate the neohexene. The separation can be performed in various ways, discontinuously or preferably continuously. It can comprise one or more fractionation(s) of the reaction mixture, of an identical or different type, and preferably chosen from:
  fractionation by change of physical state, preferably by change of gaseous/liquid phase, in particular by distillation or by condensation,
  fractionation by molecular filtration, preferably by means of semi-permeable and selective membrane, and
  fractionation by adsorption, preferably by means of molecular sieve.

The separation can be performed in at least one fractionation zone (F) which is either distinct and separate from the reaction zone (Z), e.g. in one or more distillation/condensation column(s) or tower(s), or arranged in a part of said reaction zone (Z), e.g. in a distillation column reactor, such as described previously and in American U.S. Pat. No. 4,242, 530.

The separation can also be performed by a double (or multiple) fractionation of the reaction mixture, comprising a combination of two (or more) successive fractionations, in particular of an identical or different type, preferably chosen from the three above-mentioned types of fractionation. More particularly, the separation can be performed in two (or more) successive fractionation zones, e.g. either at least one fractionation zone arranged inside the reaction zone (Z) and the other one(s) outside said reaction zone (Z), e.g. successively in a distillation column reactor and then in at least one distillation/condensation column or tower, or all of them arranged outside the reaction zone (Z), e.g. in two or more distillation/condensation columns or towers, so as in particular preferably to separate and to isolate the neohexene and at least one of the other components of the reaction mixture, preferably the 2,3-dimethyl-2-butene, the 2,3-dimethyl-1-butene and/or the unreacted isobutene which is then preferably recycled into the contacting with the catalyst.

The process of the invention can be advantageously performed by means of a distillation column reactor, as described above, comprising both a reaction zone and a fractionation zone. In the reaction zone of said reactor, the isobutene can be contacted with the catalyst, preferably continuously, so as to form the reaction mixture preferably in the form of a mixed gaseous/liquid phase, and simultaneously in the fractionation zone of said reactor, one or more component(s) of said reaction mixture is (are) preferably continuously separated, in particular ethylene, unreacted isobutene and preferably neohexene, so as particularly to isolate the neohexene and more particularly the unreacted isobutene which is then preferably recycled into said reaction zone.

The fractionation by change of the physical state, preferably of the gaseous/liquid phase of the reaction mixture, can be performed in one or more distillation/condensation columns or towers, or else in a distillation column reactor, in particular by cooling or heating the reaction mixture, so as to condense or to vaporise at least one of the components of the reaction mixture, preferably neohexene, and preferably to separate it and to isolate it from the rest of the mixture. The fractionation can in particular be performed by distillation of the reaction mixture, more particularly in at least one distillation column or one distillation column reactor, so as to withdraw at the top of said column or reactor ethylene, then at a lower level unreacted isobutene, which is preferably recycled into the reaction zone, and at a still lower level neohexene, which can thus be separated and isolated in its turn from the rest of the liquid mixture containing in particular 2,3-dimethyl-2-butene, 2,3-dimethyl-1-butene and diisobutene. The rest of the liquid mixture can be then subjected to a fractionation in its turn, in particular by distillation, so as to separate and to isolate the 2,3-dimethyl-2-butene and/or the 2,3-dimethyl-1-butene from the diisobutene, thus upgrading the process, since 2,3-dimethyl-2-butene and/or 2,3-dimethyl-1-butene are sought-after products because of their relatively high octane number.

The fractionation by molecular filtration can be performed by passing the reaction mixture through one or more semi-permeable and selective membrane(s), so as to arrest at least one of the components of the reaction mixture, preferably the neohexene, and to allow the rest of the reaction mixture, in particular the ethylene, the 2,3-dimethyl-2-butene, the 2,3-dimethyl-1-butene, the diisobutene and optionally the unreacted isobutene, to pass through.

The fractionation by adsorption can be performed by passing the reaction mixture onto one or more molecular sieves, so as to retain at least one of the components of the reaction mixture, preferably the neohexene, and to allow the other component(s) of the reaction mixture, in particular the ethylene, the 2,3-dimethyl-2-butene, the 2,3-dimethyl-1-butene, the diisobutene and optionally the unreacted isobutene, to pass through, and by subjecting the component(s) of the reaction mixture thus retained to at least one desorption step, preferably by the TSA method ("Temperature Swing Adsorption") or the PSA method ("Pressure Swing Adsorption"), so as to isolate it (or them).

The separation can also comprise a combination of at least two or three successive fractionations of a different type, preferably chosen from the three above-mentioned fractionations, so as in particular preferably to separate (a) neohexene and at least one of the following other components of the reaction mixture: (b) 2,3-dimethyl-1-butene, (c) 2,3-dimethyl-2-butene, (d) diisobutene, (e) ethylene and (f) unreacted isobutene.

The process can advantageously comprise separating unreacted isobutene from the reaction mixture, and then preferably recycling it into the contacting with the catalyst, so as in particular to increase the output of the process. The process can also comprise separating 2,3-dimethyl-1-butene and/or 2,3-dimethyl-2-butene from the reaction mixture, and preferably isolating it (or them), in particular by reason of its (their) relatively high octane number.

The process can advantageously comprise separating and isolating the $C_{5+}$ hydrocarbon products (i.e. comprising at least 5 carbon atoms), e.g. $C_{5+}$ olefins and optionally $C_{5+}$ alkane(s), including neohexene, from the reaction mixture as a single component, so as in particular to blend said single component with gasoline to enhance the gasoline octane number, or in particular to use said single component as a gasoline blendstock.

The present invention also relates to the use of the previously mentioned single component for blending it with gasoline to enhance the gasoline octane number. It also relates to the use of the previously mentioned single component as a gasoline blendstock. The process can also advantageously comprise separating the $C_{5+}$ hydrocarbon products, e.g. $C_{5+}$ olefins and optionally $C_{5+}$ alkane(s), including neohexene, from the reaction mixture as a single component, followed by separating and isolating at least one separated fraction from said single component, so as in particular to blend said at least one separated fraction with gasoline to enhance the gasoline octane number, or in particular to use said at least one separated fraction as a gasoline blendstock.

The present invention also relates to the use of the at least one previously mentioned separated fraction, for blending it with gasoline to enhance the gasoline octane number. It also relates to the use of the at least one previously mentioned separated fraction as a gasoline blendstock.

The process of the invention is also particularly advantageous for manufacturing neohexene, namely in a single (reaction) stage and with a relatively high specificity.

The following examples illustrate the present invention.

EXAMPLE 1

Preparation of a Metal Catalyst Comprising an Organometallic Tungsten Hydride Grafted onto Alumina (W—H/Al)

In a first stage, 2.5 g of an γ-alumina sold under the trade reference "Aeroxide® Alu C" by Degussa (Germany), having a specific surface area (B.E.T.) of 100 m²/g and containing 94.95 wt % of alumina and 5 wt % of water, were subjected to a calcination treatment at 500° C. under an air current for 15 hours, then to a dehydroxylation treatment at 500° C. under an absolute pressure of $10^{-2}$ Pa for 15 hours. The alumina thus treated exhibited in infrared spectroscopy three absorption bands, at 3774, 3727 and 3683 cm$^{-1}$ respectively, characteristic of residual (AlO—H) bonds.

In a second stage, 1.8 g of the alumina prepared beforehand were isolated and introduced at 25° C. under an argon atmosphere into a reactor fitted with a means of agitation. Then, 305 mg of tungsten tris(neopentyl)neopentylidyne, acting as a precursor (Pr) of the catalyst, were introduced into the reactor, said precursor having the general formula (24):

$$W[-CH_2-C(CH_3)_3]_3[\equiv C-C(CH_3)_3] \quad (24)$$

The reactor was then heated to 66° C. and the mixture thus obtained was agitated in the dry state for 4 hours, so as to obtain an organometallic tungsten compound grafted onto the alumina. At the end of this time, the reactor was cooled to 25° C. and the surplus of unreacted precursor (Pr) was removed by washing of the mixture with n-pentane at 25° C. The organometallic tungsten compound grafted onto the alumina was then vacuum dried, and then isolated under an argon atmosphere. It contained 4.4 wt % of tungsten and complied with the general formula (25):

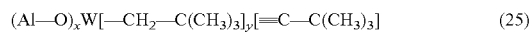

$$(Al-O)_xW[-CH_2-C(CH_3)_3]_y[\equiv C-C(CH_3)_3] \quad (25)$$

with x=1 et y=2.

In a third stage, 500 mg of the organometallic tungsten compound grafted onto the alumina prepared beforehand were placed in a reactor with a capacity of 500 ml in order to perform a hydrogenolysis treatment by contacting said compound with hydrogen, under a hydrogen absolute pressure of 73 kPa, at 150° C. for 15 hours. At the end of this time, the reactor was cooled to 25° C., and there was obtained and isolated under an argon atmosphere at atmospheric pressure a catalyst (W—H/Al) comprising an organometallic tungsten hydride grafted onto alumina. The catalyst contained 4.4 wt % of tungsten and exhibited in infrared spectroscopy two absorption bands at 1903 and 1804 cm$^{-1}$ respectively, characteristic of the (W—H) bond grafted onto the alumina. In addition, it exhibited in nuclear magnetic resonance (solid $^1$H-NMR) under 500 MHz a value for the chemical shift of the tungsten hydride ($\delta_{W-H}$) of 0.6 ppm (parts per million).

EXAMPLE 2 (comparative)

Preparation of a Metal Catalyst Comprising an Organometallic Tantalum Hydride Grafted onto Silica (Ta—H/Si)

In a first stage, 1.8 of a silica sold under the trade reference "Aerosil 200200 " by Degussa (Germany), having a specific surface area (B.E.T.) of 200 m²/g, were subjected to a dehydroxylation treatment at 500° C. under an absolute pressure of $10^{-2}$ Pa for 15 hours. The silica thus obtained exhibited in infrared spectroscopy an absorption band at 3747 cm$^{-1}$, characteristic of the residual (SiO—H) bond.

In a second stage, 1.4 g of the silica prepared beforehand were isolated and introduced at 25° C. under an argon atmosphere into a reactor fitted with a means of agitation. Then, 15 ml of n-pentane containing 270 mg of tantalum tris(neopentyl)-neopentylidene, acting as a precursor (Pr') of the catalyst, were introduced into the reactor, said compound having the general formula (26):

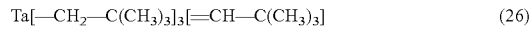

$$Ta[-CH_2-C(CH_3)_3]_3[\equiv CH-C(CH_3)_3] \quad (26)$$

The mixture thus obtained was agitated at 25° C. for 2 hours, so as to obtain an organometallic tantalum compound grafted onto the silica. At the end of this time, the surplus of unreacted precursor (Pr') was removed by washing with n-pentane at 25° C. The organometallic tantalum compound grafted onto the silica was then vacuum dried. It contained 5.2 wt % and complied with general formulae (27) and (28):

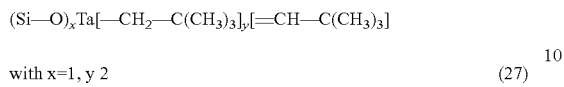

with x=1, y 2 (27)

and with x=2, y=1 (28)

In a third stage, the organometallic tantalum compound grafted onto silica prepared beforehand was subjected to a hydrogenolysis treatment by contacting of said compound with hydrogen, under a hydrogen absolute pressure of 73 kPa, at 150° C. for 15 hours. At the end of this time, there was obtained and isolated under an argon atmosphere a catalyst (Ta—H/Si) comprising an organometallic tantalum hydride grafted onto silica. The catalyst contained 5.2 wt % of tantalum and exhibited in infrared spectroscopy an absorption band at 1830 cm$^{-1}$, characteristic of the (Ta—H) bond grafted onto the silica.

EXAMPLE 3

Preparation of Neohexene with the (W—H/Al) Catalyst

Isobutene was introduced continuously into a dynamic reactor with a capacity of 5 ml, heated to 150° C. and containing 500 mg of the (W—H/Al) catalyst prepared in Example 1, at a rate of 1.52 moles of isobutene per mole of tungsten of the catalyst and per minute, under a total absolute pressure of 0.1 MPa. It was observed that initially the rate of conversion of the isobutene was of the order of 40% and that after 300 minutes of the contacting, the rate of conversion was stabilised at around 10%. The reaction mixture obtained after 500 minutes of the contacting comprised neohexene, 2,3-dimethyl-2-butene, ethylene, diisobutene and unreacted isobutene. The following molar selectivities were then measured and calculated:
neohexene: 21%,
2,3-dimethyl-1-butene: 33%
2,3-dimethyl-2-butene: 8%.
ethylene: 30%
diisobutene: 8%

At the end of 1000 minutes of the contacting, a quantity of hydrogen was added into the reactor such that the molar proportion of hydrogen in the reactor was 4.5%. The rate of conversion of the isobutene increased immediately from 10% to 23% and then stabilised at this latter value.

After 1200 minutes of the contacting, the reactor was cooled to 20° C., the introduction of isobutene was stopped, the reaction mixture was recovered and the neohexene was isolated from the rest of the mixture by micro-distillation.

EXAMPLE 4 (comparative)

Preparation of Neohexene with the (Ta—H/Si) Catalyst

Exactly the same procedure was adopted as in Example 3, except that instead of the (W—H/Al) catalyst, the (Ta—H/Si) catalyst prepared in Example 2 (comparative) was used. It was observed that initially the rate of conversion of the isobutene was of the order of 12% and that after 300 minutes of the contacting it stabilised at around 1.5%. The mixture obtained after 500 minutes of the contacting comprised neohexene, 2,3-dimethyl-2-butene, ethylene, propene, isopentene, diisobutene and unreacted isobutene. The following molar selectivities were then measured and calculated:
neohexene: 2%,
2,3-dimethyl-1-butene: 32%
2,3-dimethyl-2-butene: 9%
ethylene: 20%
isopentene: 22%
propene: 10%
diisobutene: 5%

It was found that the molar selectivity for neohexene was very weak (about 10 times weaker than that obtained in Example 3), and that other different olefins were formed, in particular isopentene and propene.

The invention claimed is:

1. Process for manufacturing neohexene, comprising contacting isobutene with a supported metallic catalyst comprising a tungsten compound selected from the group consisting of from tungsten hydrides, organometallic tungsten compounds and organometallic tungsten hydrides, and a support comprising an oxide of aluminium, so as to form a reaction mixture comprising neohexene.

2. Process according to claim 1, wherein the catalyst comprises a support comprising an oxide of aluminium onto which is grafted the tungsten compound.

3. Process according to claim 1, wherein the support is selected from the group consisting of simple oxides of aluminium, mixed oxides of aluminium and oxides of aluminium modified by one or more elements of Groups 13 to 17 of the Periodic Table of the Elements.

4. Process according to claim 1, wherein the support is selected from the group consisting of porous aluminas, semi-porous aluminas, non-porous aluminas and mesoporous aluminas.

5. Process according to claim 1, wherein the support is a porous or non-porous alumina selected from the group consisting of a γ-alumina (gamma-alumina), an η-alumina (eta-alumina), a δ-alumina (delta-alumina), a θ-alumina (theta-alumina), a κ-alumina (kappa-alumina) a ρ-alumina (ro-alumina), a χ-alumina (ksi or -chi-alumina) and an α- alumina (alpha-alumina).

6. Process according to claim 1, wherein the tungsten compound is selected from the group consisting of the organometallic tungsten compounds and the organometallic tungsten hydrides comprise one or more hydrocarbon radicals, either identical or different, linear or branched, saturated or unsaturated.

7. Process according to claim 1, wherein the tungsten compound comprises one or more ligands, being identical or different, comprising at least one oxygen atom and/or at least one nitrogen atom.

8. Process according to claim 7, wherein the ligand is selected from the group consisting of oxo, alkoxo, aryloxo, aralkyloxo, nitrido, imido and amido ligands.

9. Process according to claim 1, wherein the contacting is performed at a temperature chosen in a range of from 50 to 600 ° C.

10. Process according to claim 1, wherein the contacting is performed under a total absolute pressure chosen in a range of from 0.01 to 100 MPa.

11. Process according to claim 1, wherein the contacting is performed with quantities of isobutene and catalyst such that the molar ratio of isobutene to tungsten of the catalyst is chosen in a range of from 1 to $10^7$.

12. Process according to claim 1, wherein the contacting is performed in a reaction zone containing the catalyst and into which the isobutene is introduced.

13. Process according to claim 12, wherein the isobutene is introduced into the reaction zone at a molar rate of introduction of isobutene per mole of tungsten of the catalyst and per minute chosen in a range of from 0.1 to $10^5$.

14. Process according to claim 1, wherein the contacting is performed in the presence of hydrogen.

15. Process according to claim 14, wherein the contacting is performed under a hydrogen partial pressure chosen in a range of from 0.1 kPa to 10 MPa.

16. Process according to claim 1, wherein the neohexene is separated from the reaction mixture by one or more successive fractionations of said reaction mixture, of an identical or different type.

17. Process according to claim 16, wherein the separation of the neohexene is performed in one or more distillation/condensation column(s) or tower(s).

18. Process according to claim 16, wherein the separation of the neohexene is performed in a distillation column reactor.

19. Process according to claim 1, wherein the neohexene is separated from the reaction mixture in at least one fractionation zone which is either distinct and separate from the reaction zone, or arranged in a part of the reaction zone.

20. Process according to claim 1, wherein the process comprises separating unreacted isobutene from the reaction mixture, and then recycling it into the contacting with the catalyst.

21. Process according to claim 1, wherein the process comprises separating and isolating the $C_{5+}$ hydrocarbon products including neohexene as a single component from the reaction mixture.

22. Process according to claim 21, wherein the process in addition comprises blending said single component with gasoline to enhance the gasoline octane number, or using said single component as a gasoline blendstock.

23. Process according to claim 1, wherein the process comprises separating the $C_{5+}$ hydrocarbon products including neohexene from the reaction mixture as a single component, followed by separating and isolating at least one separated fraction from said single component, so as to blend said at least one separated fraction with gasoline to enhance the gasoline octane number, or to use said at least one separated fraction as a gasoline blendstock.

* * * * *